United States Patent [19]

Cobb

[11] Patent Number: 4,766,103

[45] Date of Patent: Aug. 23, 1988

[54] PREPARATION OF 1,4-DICHLOROBENZENE

[75] Inventor: Raymond L. Cobb, Bartlesville, Okla.

[73] Assignee: Phillips Petroleum Company, Bartlesville, Okla.

[21] Appl. No.: 106,760

[22] Filed: Oct. 8, 1987

Related U.S. Application Data

[62] Division of Ser. No. 883,578, Jul. 7, 1986, Pat. No. 4,727,201.

[51] Int. Cl.$^4$ .............. B01J 27/053; B01J 27/08; B01J 27/125; B01J 27/138

[52] U.S. Cl. .................. 502/217; 502/224; 502/226; 502/231; 423/463; 423/466; 423/468; 423/490; 423/495; 423/497; 423/500; 423/554

[58] Field of Search .............. 502/224, 226, 231, 217; 423/463, 466, 490, 495, 497, 500, 468, 554

[56] References Cited

U.S. PATENT DOCUMENTS

| | | | |
|---|---|---|---|
| 2,381,562 | 8/1945 | Stewart | 502/231 |
| 2,399,488 | 4/1946 | Hearne | 502/231 |
| 2,429,232 | 10/1947 | Latchum, Jr. et al. | 502/224 |
| 2,666,085 | 1/1954 | Fitzpatrick | 260/650 |
| 2,727,075 | 12/1955 | Mattano | 260/650 |
| 2,920,110 | 1/1960 | Kolka et al. | 260/650 |
| 3,214,482 | 10/1965 | Caropreso et al. | 260/659 |
| 3,226,447 | 12/1965 | Bing et al. | 260/650 |
| 3,425,798 | 2/1969 | Statman et al. | 423/500 |
| 3,496,217 | 2/1970 | Drinkard, Jr. et al. | 260/465.8 |
| 3,526,531 | 9/1970 | Asano et al. | 117/62.2 |
| 3,576,867 | 4/1971 | Schoot | 260/558 |
| 3,636,171 | 1/1972 | Krumel et al. | 260/650 R |
| 3,760,014 | 9/1973 | Haskett | 260/650 R |
| 3,816,526 | 6/1974 | Jurewicz | 260/544 M |
| 3,832,452 | 8/1974 | Crouch, Jr. | 423/495 |
| 3,883,604 | 5/1975 | Rudolph et al. | 260/653.1 T |
| 3,939,247 | 2/1976 | Fougner | 423/495 |
| 4,017,551 | 4/1977 | Milam et al. | 260/650 R |
| 4,025,516 | 5/1977 | Razdan et al. | 260/345.3 |
| 4,111,991 | 9/1978 | Garrison | 423/497 |
| 4,294,996 | 10/1981 | Wetzel et al. | 568/776 |
| 4,376,220 | 3/1983 | Wetzel et al. | 568/776 |
| 4,446,075 | 5/1984 | Eiglmeier et al. | 260/465 G |
| 4,487,846 | 12/1984 | Bailly et al. | 502/154 |
| 4,497,904 | 2/1985 | Blaya et al. | 502/226 |
| 4,567,153 | 1/1986 | Graves | 502/226 |
| 4,575,538 | 3/1986 | Hsieh et al. | 525/244 |
| 4,727,201 | 2/1988 | Cobb | 570/202 |

*Primary Examiner*—Anthony McFarlane
*Attorney, Agent, or Firm*—K. K. Brandes

[57] ABSTRACT

1,2-dichlorobenzene is isomerized to 1,4-dichlorobenzene in the presence of a catalyst comprising (a) at least one of AlCl$_3$ and AlBr$_3$ and (b) at least one of iodine, alkaline earth metal halides and sulfates and lanthanide halides. Benzene and/or dichlorobenzene is chlorinated with free chlorine in the presence of a catalyst composition comprising (a) at least one suitable metal halide (preferably AlCl$_3$, SbCl$_5$ or FeCl$_3$) and (b) free iodine and/or at least one organic iodo-compound (preferably methyl iodide of p-iodochlorobenzene), so as to obtain a reaction product comprising 1,4-dichlorobenzene. A preferred catalyst composition comprises (a) at least one of AlCl$_3$ and AlBr$_3$, (b) free iodine and (c) at least one of alkaline earth metal halides, alkaline earth metal sulfates and lanthanide halides.

10 Claims, No Drawings

PREPARATION OF 1,4-DICHLOROBENZENE

This application is a division of pending application Ser. No. 882,578, filed July 7, 1986, now allowed.

BACKGROUND OF THE INVENTION

In one aspect, this invention relates to a process for converting 1,2-dichlorobenzene (ortho-dichlorobenzene) to 1,4-dichlorobenzene (para-dichlorobenzene). In another aspect, this invention relates to a process for chlorinating benzene and/or chlorobenzene so as to produce 1,4-dichlorobenzene at good selectivity. In a further aspect, this invention relates to modified Friedel-Crafts catalysts for preparing 1,4-dichlorobenzene.

It is known to produce 1,4-dichlorobenzene, generally in conjunction with 1,3-dichlorobenzene, by isomerization of 1,2-dichlorobenzene in the presence of a Friedel-Crafts catalyst such as $AlCl_3$. It is also known to produce 1,4-dichlorobenzene by chlorination of benzene or chlorobenzene in the presence of Friedel-Crafts catalysts such as chlorides of Al, Sb and Fe. However, there is an ever present need to develop new processes for producing 1,4-dichlorobenzene at higher selectivity by employing more effective catalysts than those presently known. 1,4-dichlorobenzene is used as a monomer for preparing poly(phenylene sulfide).

SUMMARY OF THE INVENTION

It is an object of this invention to at least partially convert 1,2-dichlorobenzene (o-dichlorobenzene) to 1,4-dichlorobenzene (p-dichlorobenzene). It is another object of this invention to convert benzene and/or chlorobenzene to 1,4-dichlorobenzene at high selectivity. It is a further object of this invention to use modified, improved Friedel-Crafts catalysts in the above-identified reactions for enhanced selectivity to 1,4-dichlorobenzene. It is another object to provide a new catalyst composition useful for converting 1,2-dichlorobenzene to 1,4-dichlorobenzene at high selectivity. Other objects and advantages will be apparent from the detailed description and the appended claims.

In accordance with this invention, a feed stream comprising 1,2-dichlorobenzene is contacted with a catalyst composition (selective for the production of 1,4-dichlorobenzene) comprising
(a) at least one aluminum halide selected from the group consisting of $AlCl_3$ and $AlBr_3$, and
(b) at least one substance selected from the group consisting of free iodine, alkaline earth metal sulfates, alkaline earth metal halides and lanthanide halides, under such reaction conditions as to convert at least a portion of 1,2-dichlorobenzene to 1,4-dichlorobenzene.

Also in accordance with this invention, an aromatic feed stream comprising at least one aromatic compound selected from the group consisting of benzene and chlorobenzene is contacted with a free chlorine containing stream and a catalyst composition (selective for the production of 1,4-dichlorobenzene) comprising
(a) at least one metal chloride selected from the group consisting of chlorides of Al, Ge, Sn, Sb, Bi, Ti, Zr, Hf, V, Cr, Mo, W, Mn, Re, Fe, Co, Ni, Cu, Zr and Cd,
(b) at least one iodine-containing substance selected from the group consisting of free iodine and organic iodo-compounds (preferably methyl iodide or p-iodochlorobenzene),
under such contacting conditions as to obtain a product stream comprising 1,4-dichlorobenzene; wherein the mol ratio of chlorine in said free chlorine containing stream to catalyst component (b) is in the range of from about 4:1 to about 1000:1.

Preferably, catalyst component (a) is at least one of $AlCl_3$, $SbCl_5$ and $FeCl_3$. The presently preferred organic feed compound is chlorobenzene.

Further in accordance with this invention, a composition of matter (useful as a catalyst for isomerizing orthoto paradichlorobenzene) comprises (preferably consists essentially of) a mixture of:
(a) at least one aluminum halide selected from the group consisting of $AlCl_3$ and $AlBr_3$ (preferably $AlCl_3$),
(b) free iodine, and
(c) at least one substance selected from the group consisting of alkaline earth metal halides (preferably $MgF_2$, $MgCl_2$ and $MgBr_2$), alkaline earth metal sulfates (preferably $MgSO_4$) and lanthanide halides. Particularly preferred as catalyst compound (c) are lanthanide halides, most preferably $LaCl_3$, $CeCl_3$, $SmCl_3$, $GdCl_3$ and $ErCl_3$.

DETAILED DESCRIPTION OF THE INVENTION

Preparation of 1,4-dichlorobenzene by Isomerization

Any feed stream which contains 1,2-dichlorobenzene (o-DCB) can be used in the conversion of o-DCB to p-DCB (1,4-dichlorobenzene). The feed stream may contain suitable diluents. Preferably, undiluted liquid o-DCB is used as feed. The o-DCB containing feed stream can be contacted with the catalyst composition, in accordance with this invention, in any suitable manner. The isomerization process of this invention can be carried out as a continuous process or as a batch process, preferably with agitation (e.g., by means of mechanical stirring means or static mixing means).

The catalyst composition, which is employed in the isomerization process of this invention, comprises two components: (a) $AlCl_3$ or $AlBr_3$ or mixtures thereof (preferably $AlCl_3$), and (b) one or more substances selected from the group consisting of free iodine, sulfates of alkaline earth metals (preferably $MgSO_4$), halides of alkaline earth metals (preferably $MgF_2$, $MgCl_2$ and $MgBr_2$), halides of lanthanide metals (preferably $LaCl_3$, $CeCl_3$, $NdCl_3$, $SmCl_3$, $GdCl_3$ and $ErCl_3$).

More preferably, catalyst component (b) comprises a mixture of iodine and at least one other substance selected from the group consisting of halides of alkaline earth metals, sulfates of alkaline earth metals and halides of lanthanides. Examples of such preferred catalyst components (b) are: $I_2+MgSO_4$, $I_2+MgCl_2$, $I_2+MgF_2$, $I_2+LaCl_3$, $I_2+CeCl_3$, $I_2+NdCl_3$, $I_2+SmCl_3$, $I_2+GdCl_3$, $I_2+ErCl_3$, $I_2+MgSO_4+LaCl_3$, $I_2+MgCl_2+SmCl_3$ and other mixtures of $I_2$, alkaline earth metal halide or sulfate and lanthanide halide.

The weight ratio of catalyst component (a) to catalyst component (b) can range from about 1:10 to about 100:1, preferably from about 1:2 to about 20:1. Catalyst components (a) and (b) can be mixed in any suitable manner and can be brought in contact with the o-DCB containing feed in any suitable manner. Components (a) and (b) can be premixed and then contacted with the feed. Or catalyst components (a) and (b) can be charged separately to a reactor, mixed and then contacted with the o-DCB containing feed.

In the particularly preferred catalyst composition comprising (a) at least one of AlCl$_3$ and AlBr$_3$, (b) iodine and (c) at least one of halides of alkaline earth metals, sulfates of alkaline earth metals and halides of lanthanides, the weight ratio of component (a) to component (b) is generally in the range of from about 1:5 to about 50:1 (more preferably about 1:2 to about 20:1), and the weight ratio of component (b) to component (c) is in the range of from about 1:20 to about 20:1 (more preferably from about 1:5 to about 5:1). Components (a), (b) and (c) can be mixed in any order and by any mixing means, preferably by milling, more preferably under an inert gas atmosphere.

In a continuous operation, preferably the o-DCB containing feed stream, a stream of catalyst component (a) and a stream of catalyst component (b) are metered separately and are continuously charged to a reactor. These three streams are then mixed by mechanical stirring or static mixing means while they flow through the reactor (in a downflow or upflow or horizontal direction) under reaction conditions. The weight ratio of o-DCB in the feed to the catalyst composition (i.e., the sum of the two catalyst components) can range from about 1000:1 to about 1:1, preferably from about 100:1 to about 10:1.

Any suitable reaction conditions can be employed in the isomerization process of this invention. The reaction temperature can be in the range of from about 40° C. to about 250° C., preferably from about 80° C. to about 180° C. The reaction pressure can be subatmospheric, atmospheric (i.e., about 1 atm) or superatmospheric. Generally the reaction pressure is about atmospheric. Any suitable reaction time, i.e., time of intimate contact between feed and catalyst components (a) and (b), can be employed. The reaction time can range from about 0.1 hours to about 50 hours, depending on the reaction temperature, the degree of agitation and specific catalyst used, and will preferably be in the range of from about 0.5 hour to about 5 hours.

Any formed product, primarily p-dichlorobenzene (p-DCB), can be separated from unreacted o-DCB, from catalyst components (a) and (b) and from other formed products by any suitable separation means, preferably by fractional distillation. Unreacted o-DCB can be recycled to the reactor.

Preparation of 1,4-dichlorobenzene by Chlorination

Any aromatic feed stream which contains benzene or chlorobenzene or a mixture of both can be used in the chlorination process of this invention. The feed stream may contain suitable diluents. Preferably undiluted liquid chlorobenzene is used as aromatic feed. The aromatic feed stream can be contacted with a chlorine containing stream and the catalyst composition, in accordance with the chlorination process of this invention, in any suitable manner. The free chlorine containing stream can contain gaseous chlorine or liquid chlorine. The chlorination process of this invention can be carried out as a continuous process or a batch process, preferably with agitation (e.g., by means of mechanical or static mixing means). The aromatic feed stream and the free chlorine containing stream can be premixed, or they can be charged separately in any order to a reactor and then substantially mixed in the reactor.

The catalyst composition, which is selective for producing 1,4-dichlorobenzene when employed in the chlorination process of this invention, comprises two components: (a) one or more metal chlorides as defined above in the Summary of the Invention (preferably at least one of AlCl$_3$, FeCl$_3$ and SbCl$_5$), and (b) iodine or one or more organic iodo-compounds, or mixtures thereof, more preferably I$_2$. Suitable organic iodo-compounds having the general formula R-I can be employed, wherein R can be a linear or branched alkyl group, preferably having from 1 to 6 C atoms per molecule (more preferably the methyl group), or an unsubstituted cycloalkyl or alkyl-substituted cycloalkyl group (such as the cyclohexyl group) having from 6 to 12 carbon atoms per molecule, or an unsubstituted aryl (such as the phenyl group), alkyl-substituted aryl group (such as the tolyl group) or halogen-substituted aryl group (preferably the 4-chlorophenyl group) having from 6 to 12 carbon atoms per molecule.

The weight ratio of catalyst component (a) to catalyst component (b) generally ranges from about 1:10 to about 100:1, and preferably is in the range of from about 1:1 to about 20:1. Catalyst components (a) and (b) can be mixed in any suitable manner and can be brought into contact with the aromatic feed stream and the chlorine containing stream in any suitable manner. Components (a) and (b) can be premixed or they can be charged in any order to a reactor where they are mixed and contacted with the aromatic feed stream and the free chlorine containing stream.

In a continuous operation, the aromatic feed stream, the free chlorine containing feed stream, a stream of catalyst component (a) and a stream of catalyst component (b) are metered separately and are continuously charged to a reactor. These feed streams are then mixed by mechanical stirring or by static mixing means while they flow through the reactor in any direction (upflow, downflow or horizontal), under reaction conditions.

The weight ratio of the aromatic feed compound (benzene or chlorobenzene or both) to free chlorine can range from about 1:20 to about 200:1, and is preferably in the range of from about 1:1 to about 10:1. When the preferred feed compound, chlorobenzene, is employed, this weight ratio range is more preferably from about 1:1 to about 3:1. The weight ratio of the aromatic feed compound to the catalyst composition (i.e., the sum of the two catalyst components) can range from about 3:1 to about 1000:1, preferably for about 10:1 to about 100:1. In order to minimize the formation of aromatic iodo-compounds, it is necessary to employ a mol ratio of free chlorine to catalyst component (b) in the range of from about 4:1 to about 1000:1, preferably from about 5:1 to about 100:1.

Any suitable reaction temperature can be employed in the chlorination process of this invention. Generally, the reaction temperature is in the range of from about 10° C. to about 150° C., preferably from about 40° C. to about 60° C. The reaction pressure can be subatmospheric, atmospheric (preferred) or superatmospheric. Any suitable reaction time, i.e., the time of intimate contact between aromatic feed stream, free chlorine containing stream and catalyst components (a) and (b), can be employed. The reaction time can range from about 1 second to about 50 hours, depending on the temperature, the degree of agitation and the specific catalyst composition used, and will preferably be in the range of from about 3 seconds to about 1 hour.

Any formed product, primarily p-dichlorobenzene, can be separated from unreacted aromatic feed, from catalyst components (a) and (b) and from other formed products (such as iodine-containing by-products) in any suitable manner, preferably by fractional distillation.

Unreacted aromatic feed and chlorine can be recycled to the reactor.

The following examples are presented for further illustration of the invention and are not to be considered as unduly limiting the scope of this invention.

fate (when used); about 2 grams of iodine (when used); about 1 gram of lanthanide chloride (when used). The various catalyst components were manually mixed under a dry nitrogen atmosphere. Pertinent test results are summarized in Table I.

TABLE I

| Run | Catalyst | % Conversion of o-DCB | Product Distribution (Wt %) | | | | Ratio p-DCB/m-DCB |
| | | | o-DCB | p-DCB | m-DCB[1] | CB[2] | |
|---|---|---|---|---|---|---|---|
| 1 (Control) | $AlCl_3$ | 10 | 90.3 | 1.8 | 7.8 | — | 0.24 |
| 2 (Control) | $AlCl_3$ | 10 | 89.9 | 1.9 | 8.1 | — | 0.24 |
| 3 (Control) | $AlCl_3$ | 6 | 94.1 | 1.5 | 4.3 | — | 0.36 |
| 4 (Invention) | $AlCl_3 + I_2$ | 21 | 79.4 | 4.5 | 3.0 | 5.2 | 1.49 |
| 5 (Invention) | $AlCl_3 + I_2$ | 17 | 83.2 | 3.2 | 3.2 | 5.5 | 1.01 |
| 6 (Invention) | $AlCl_3 + I_2$ | 29 | 71.3 | 6.1 | 5.1 | 7.5 | 1.21 |
| 7 (Control) | $AlBr_3$ | 5 | 94.6 | 0 | 4.6 | — | 0 |
| 8 (Invention) | $AlBr_3 + I_2$ | 15 | 84.5 | 5.2 | 0.9 | — | 0.17 |
| 9 (Invention) | $AlBr_3 + MgSO_4$ | 12 | 88 | 1.7 | 9.5 | — | 0.18 |
| 10 (Invention) | $AlBr_3 + MgSO_4 + I_2$ | 33 | 67 | 1.8 | 8.5 | — | 0.21 |
| 11 (Invention) | $AlCl_3 + MgSO_4$ | 21 | 79.0 | 4.1 | 16.4 | 0.3 | 0.25 |
| 12 (Invention) | $AlCl_3 + MgSO_4 + I_2$ | 42 | 57.8 | 10.6 | 8.2 | 9.3 | 1.28 |
| 13 (Invention) | $AlCl_3 + MgCl_2$ | 15 | 85 | 2.2 | 13 | — | 0.17 |
| 14 (Invention) | $AlCl_3 + MgCl_2 + I_2$ | 35 | 65 | 9.7 | 6.1 | — | 1.60 |
| 15 (Invention) | $AlCl_3 + MgF_2$ | 20 | 80 | 3.1 | 17 | — | 0.18 |
| 16 (Invention) | $AlCl_3 + MgF_2 + I_2$ | 38 | 62 | 8.8 | 7.6 | — | 1.15 |
| 17 (Invention) | $AlCl_3 + MgBr_2 + I_2$ | 33 | 67 | 6.8 | 6.2 | — | 1.10 |
| 18 (Invention) | $AlCl_3 + LaCl_3$ | 53 | 47.2 | 12.8 | 38.0 | 1.1 | 0.34 |
| 19 (Invention) | $AlCl_3 + LaCl_3 + I_2$ | 66 | 34.5 | 17.6 | 16.5 | 14.2 | 1.06 |
| 20 (Invention) | $AlCl_3 + CeCl_3$ | 73 | 27.1 | 20.6 | 19.7 | 15.0 | 1.05 |
| 21 (Invention) | $AlCl_3 + CeCl_3 + I_2$ | 74 | 28.1 | 24.5 | 14.0 | 14.3 | 1.76 |
| 22 (Invention) | $AlCl_3 + CeCl_3 + I_2$ | 66 | 34.0 | 18.9 | 16.0 | 13.6 | 1.18 |
| 23 (Invention) | $AlCl_3 + NdCl_3$ | 62 | 38.2 | 15.7 | 41.0 | 2.4 | 0.38 |
| 24 (Invention) | $AlCl_3 + NdCl_3 + I_2$ | 74 | 26.2 | 19.0 | 22.2 | 15.1 | 0.85 |
| 25 (Invention) | $AlCl_3 + SmCl_3$ | 61 | 39.1 | 15.6 | 42.4 | 1.6 | 0.37 |
| 26 (Invention) | $AlCl_3 + SmCl_3 + I_2$ | 79 | 21.5 | 21.7 | 23.5 | 16.0 | 0.92 |
| 27 (Invention) | $AlCl_3 + GdCl_3$ | 65 | 34.9 | 17.0 | 44.4 | 1.9 | 0.38 |
| 28 (Invention) | $AlCl_3 + GdCl_3 + I_2$ | 75 | 25.0 | 20.9 | 21.5 | 14.2 | 0.97 |
| 29 (Invention) | $AlCl_3 + ErCl_3 + I_2$ | 34 | 65.6 | 7.7 | 6.2 | 8.7 | 1.23 |

[1]meta-dichlorobenzene
[2]chlorobenzene

EXAMPLE I

This example illustrates the conversion of 1,2-dichlorobenzene (o-dichlorobenzene; o-DCB) to 1,4-dichlorobenzene (p-dichlorobenzene; p-DCB), in the presence of $AlCl_3$ or $AlBr_3$ and various promoters, in accordance with this invention.

50 cc of o-DCB was stirred and heated for about 4 hours with various metal halide catalysts under a nitrogen atmosphere at about 150°–160° C. The reaction product was analyzed by gas-liquid chromatography employing a Hewlett-Packard HP5880 instrument equipped with a flame ionization detector and a capillary absorption column (length: 50 m) the inside wall of which was coated with crosslinked methylsilicone. The column was held at 50° C. for 8 minutes, and then heated at a rate of 10° C./minute to 250° C. Typical retention times under these conditions were: 9.50 minutes for chlorobenzene, 14.70 minutes for meta-dichlorobenzene, (m-DCB) 14.90 minutes for p-DCB, 15.60 minutes for o-DCB, 19.0+ minutes for tri- and tetrachlorobenzenes and iodo-chlorobenzenes.

All metal halide catalysts were anhydrous and had been stored in a desiccator under nitrogen. Typical amounts of the catalyst components were: 4–6 grams of a halide of Al (preferably about 5.0 grams of $AlCl_3$); about 2 grams of magnesium halide or magnesium sul- Data in Table I clearly show that the conversion of o-dichlorobenzene (1,2-dichlorobenzene) and the selectivity to p-dichlorobenzene (1,4-dichlorobenzene) were increased when iodine and/or magnesium halides or sulfates and/or rare earth metal chlorides were used in conjunction with an aluminum halide (preferably $AlCl_3$) as catalyst compositions. In addition, the presence of $I_2$ also enhanced the ratio of para-dichlorobenzene to meta-dichlorobenzene.

EXAMPLE II

This example illustrates the conversion of chlorobenzene to dichlorobenzenes, primarily 1,4-dichlorobenzene (p-DCB), in the presence of Friedel-Crafts catalyst which contain iodine or organic iodo-compounds as promoters, in accordance with the process of this invention.

100 cc chlorobenzene, 3–5 g of a Friedel-Crafts catalyst ($AlCl_3$ or $SbCl_5$ or $FeCl_3$), and 2–5 g of iodine or of an organic iodo-compound were added to a glass reactor. This mixture was stirred at a temperature ranging from about 10° C. to about 60° C., depending on the catalyst system used, while about 15–17 g of chlorine was introduced during a time period of about 20–30 minutes. The product was analyzed substantially in accordance with the procedure described in Example I. Test results are summarized in Table II.

TABLE II

| Run | Catalyst | | Average Temp. (°C.) | Mole Ratio $CB^1:Cl_2$ | % Conversion of $CB^1$ | % Selectivity[2] to | | | Ratio p-DCB/o-DCB |
| | Component A | Component B | | | | o-DCB | m-DCB | p-DCB | |
|---|---|---|---|---|---|---|---|---|---|
| 30 (Control) | 5 g $AlCl_3$ | — | 40 | 3.0:1 | 26 | 38.5 | 3.7 | 53.6 | 1.4 |

TABLE II-continued

| Run | Catalyst Component A | Component B | Average Temp. (°C.) | Mole Ratio $CB^1:Cl_2$ | % Conversion of $CB^1$ | % Selectivity[2] to o-DCB | m-DCB | p-DCB | Ratio p-DCB/o-DCB |
|---|---|---|---|---|---|---|---|---|---|
| 31 (Invention) | 5 g $AlCl_3$ | 2 g $I_2$ | 40 | 3.0:1 | 17 | 30.6 | 1.1 | 59.9 | 2.0 |
| 32 (Invention) | 5 g $AlCl_3$ | 5 g p-iodo-chlorbenzene | 42 | 3.0:1 | 16 | 29.9 | 1.0 | 59.9 | 2.0 |
| 33 (Control) | 5 cc $SbCl_5$ | — | 9 | 3.2:1 | 9 | 33.3 | 1.4 | 65.4 | 2.0 |
| 34 (Invention) | 5 cc $SbCl_5$ | 2 g $I_2$ | 12 | 3.0:1 | 28 | 26.5 | — | 72.3 | 2.7 |
| 35 (Invention) | 3 cc $SbCl_5$ | 2 cc methyl iodide | 10 | 3.0:1 | 24 | 24.9 | — | 71.4 | 2.9 |
| 36 (Control) | 5 g $FeCl_3$ | — | 25 | 3.0:1 | 23 | 40.2 | 2.9 | 56.8 | 1.4 |
| 37 (Invention) | 5 g $FeCl_3$ | 2 g $I_2$ | 20 | 3.0:1 | 26 | 25.6 | — | 68.3 | 2.7 |
| 38[3] (Control) | 3 g $FeCl_3$ | — | 62 | 1.3:1 | 36 | 35.3 | 2.5 | 52.7 | 1.5 |
| 39[3] (Invention) | 3 g $FeCl_3$ | 1 g $I_2$ | 60 | 1.3:1 | 48 | 29.7 | — | 62.4 | 2.1 |
| 40[3] (Invention) | 3 g $FeCl_3$ | 1 g p-iodo-chlorobenzene | 59 | 1.3:1 | 37 | 31.0 | 1.2 | 61.9 | 2.0 |

[1]chlorobenzene
[2]% yield of the particular DCB ÷ % conversion × 100
[3]chlorine was charged as gas at a rate of 1 g/min. for 30 minutes Data in Table II show that the presence of iodine or of an organic iodo-compound during the chlorination of chlorobenzene resulted in a higher selectivity to the desired para-dichlorobenzene and in a higher ratio of para-dichlorobenzene to ortho-dichlorobenzene.

Reasonable variations and modifications are possible within the scope of the disclosure and the appended claims.

I claim:

1. A composition of matter comprising a mixture of:
   (a) at least one aluminum halide selected from the group consisting of $AlCl_3$ and $AlBr_3$,
   (b) free iodine, and
   (c) at least one substance selected from the group consisting of alkaline earth metal halides, alkaline earth metal sulfates and lanthanide halides.

2. A composition of matter in accordance with claim 1, wherein said component (c) is selected from the group consisting of $MgF_2$, $MgCl_2$, $MgBr_2$ and $MgSO_4$.

3. A composition of matter in accordance with claim 1, wherein component (c) is selected from the group consisting of lanthanide chlorides.

4. A composition of matter in accordance with claim 1, wherein component (a) is $AlCl_3$ and component (c) is selected from the group consisting of $LaCl_3$, $CeCl_3$, $NdCl_3$, $SmCl_3$, $GdCl_3$ and $ErCl_3$.

5. A composition of matter in accordance with claim 1, wherein the weight ratio of component (a) to component (b) is in the range of from about 1:5 to about 50:1, and the weight ratio of component (b) to component (c) is in the range of from about 1:20 to about 20:1.

6. A composition of matter in accordance with claim 1, wherein the weight ratio of component (a) to component (b) is in the range of from about 1:2 to about 20:1, and the weight ratio of component (b) to component (c) is in the range of from about 1:5 to about 5:1.

7. A composition of matter in accordance with claim 1, wherein the weight ratio of component (a) to component (b) is in the range of from about 1:10 to about 100:1.

8. A composition of matter in accordance with claim 1, wherein the weight ratio of component (b) to component (c) is in the range of from about 1:20 to about 20:1.

9. A composition of matter in accordance with claim 1, wherein component (a) is $AlCl_3$ and component (c) is selected from the group consisting of $MgF_2$, $MgCl_2$, $MgBr_2$ and $MgSO_4$.

10. A composition of matter in accordance with claim 1 consisting essentially of components (a), (b) and (c).

* * * * *